(12) United States Patent
Arnott

(10) Patent No.: US 8,544,468 B2
(45) Date of Patent: Oct. 1, 2013

(54) SYSTEM, APPARATUS AND METHOD FOR MAINTAINING AIRWAY PATENCY AND PRESSURE SUPPORT VENTILATION

(76) Inventor: Richard J. Arnott, Pittsburgh, PA (US)

( * ) Notice: Subject to any disclaimer, the term of this patent is extended or adjusted under 35 U.S.C. 154(b) by 393 days.

(21) Appl. No.: 12/897,809

(22) Filed: Oct. 5, 2010

(65) Prior Publication Data
US 2011/0079224 A1    Apr. 7, 2011

Related U.S. Application Data

(60) Provisional application No. 61/249,323, filed on Oct. 7, 2009, provisional application No. 61/258,257, filed on Nov. 5, 2009.

(51) Int. Cl.
*A61M 16/20* (2006.01)

(52) U.S. Cl.
USPC ............. 128/205.24; 128/204.18; 128/200.24

(58) Field of Classification Search
None
See application file for complete search history.

(56) References Cited

U.S. PATENT DOCUMENTS

| | | | | |
|---|---|---|---|---|
| 5,148,802 | A | * | 9/1992 | Sanders et al. ........... 128/204.18 |
| 6,047,718 | A | * | 4/2000 | Konsky et al. ..................... 137/1 |
| 2003/0192543 | A1 | * | 10/2003 | Arnott ...................... 128/204.18 |

* cited by examiner

*Primary Examiner* — Jackie Ho
*Assistant Examiner* — Eric Bryant
(74) *Attorney, Agent, or Firm* — McKay & Associates, P.C.

(57) ABSTRACT

An assembly for modifying airflow into a nasopharyngeal airway or trachea of a patient. A valve assembly having an inlet and an outlet attaches to a traditional airflow generator. A valve seal within the assembly is operable by a solenoid and is adapted to cycle in response to a programmable controller circuit wherein upon activation of both the airflow generator and the controller circuit, pressurized air from the airflow generator continuously enters the inlet but passes out of the outlet of the assembly only when the solenoid causes the valve seal to retract and to at least partially unblock the outlet such that the pressurized air is converted into a single, repeatable burst exiting the outlet thereby modifying the traditional airflow.

16 Claims, 5 Drawing Sheets

SYSTEM, APPARATUS AND METHOD FOR MAINTAINING AIRWAY PATENCY AND PRESSURE SUPPORT VENTILATION

CROSS-REFERENCE TO RELATED APPLICATIONS

The instant application claims benefit of provisional application Ser. No. 61/249,323 filed Oct. 7, 2009 and provisional application Ser. No. 61/258,257 filed Nov. 5, 2009, the disclosures of both of which are incorporated herein by reference.

BACKGROUND

1. Field of the Invention

The invention relates to the modification of pre-existing airflow generation means to produce a pressurized airflow burst or flow of air directed into the nasopharyngeal airway or trachea of the patient as a patient's inhalation action continues or is caused to occur.

2. Description of the Related Art

Breathing disorders or respiratory related problems widely exist for conditions such as sleep apnea, ventilation support, pharmaceutical delivery systems, and manual resuscitation. Each of these conditions requires a system, method and apparatus for treatment. Several of these markets are sustained today by a related line of products each having one thing in common, namely pressurized ventilation support referred to as Positive Airway Pressure (PAP). In most cases conditions are treated by a continuous positive pressure air source or a continuous positive pressure gas source. At times there may be variations such as a bi-level positive pressure air or gas source delivered by a self contained product for comfort. Unfortunately there are several circumstances where a continuous positive pressure air or gas source is not comfortable, reasonable or useful and a standard bi-level product is cost prohibitive.

In the case of Obstructive Sleep Apnea or OSA, the gold standard remains to be a continuous positive pressure of air, which is uncomfortable to say the least. Many patients cannot tolerate the application of continuous positive airway pressure, particularly because of the discomfort associated with exhalation against a continuous positive pressure or the dryness that accompanies this type of delivery. A solution has been developed to alleviate this problem by the addition of a method and apparatus, to an existing continuous positive pressure of air, which converts a substantially constant elevated airway pressure to the patient's airway, with periodic short term reductions of the elevated airway pressure to a pressure of lesser magnitude. A further advance in such treatment involves the application of alternative high and low-level positive airway pressure wherein the low-level pressure coincides with the breath exhalation of the patient's breathing cycle.

Although more expensive devices may be available that provide relief upon exhalation, they are cost-prohibitive, designed for a single use and tightly regulated by insurance companies. In some cases no device is available at all. By providing a limited reuse/disposable add on or in some cases a durable add on regulating device, the cost, hygiene and comfort for these patients become palatable.

In addition, when different drugs, including oxygen, are delivered to a patient via continuous pressure the drug amount is difficult to regulate because breathing rates differ from patient to patient. Take the case of a comatose or mentally handicapped patient. Coordinating inhalation of drug delivery with the breathing cycle is impossible. Yet, with a bi-level attachment to oxygen or a continuous air delivery system, an appropriate treatment amount is delivered and waste is minimized.

There are several bi-level apparatus devices available. Each has a specific use and is self-contained. Some are manually manipulated. However, there is no method or device that can be added to an existing continuous positive air or gas source which will convert them for the application and delivery of bi-level positive airway pressure to a patient.

The systems, methods and apparatus disclosed in the prior art for treating patients afflicted with such maladies as sleep apnea, snoring, ventilation support and pharmaceutical delivery present a number of problems which need to be addressed. The equipment utilized in such treatment is far too limiting. In the case of sleep apnea, the air stream delivered to the patient tends to dehydrate the nasopharyngeal tissue. The unnatural sensation and discomfort experienced by the patient in overcoming the positive pressure during exhalation results in many patients abandoning the use of a system that is in all other respects quite beneficial. An alternative, much more expensive device is rejected by many insurance companies. By supplying a device as a simple add-on product it is possible to convert these devices to a comfortable useful source of treatment, as follows.

SUMMARY

It is the objective of the instant invention to provide a device which may be added to any continuous positive air pressure (CPAP) or gas source be it in the home, hospital or via emergency medical treatment.

It is further the objective of the invention to lessen the unnatural sensation and discomfort experienced by the patient in overcoming the traditional positive pressure during breath exhalation.

It is further the objective of the invention to supply the device as a simple add-on product to convert these traditional CPAP units to a useful source of treatment without considerable expense.

Accordingly, what is provided is an assembly for modifying airflow into a nasopharyngeal airway or trachea of a patient, comprising a valve assembly adapted to attach to an airflow generator, the valve assembly having two ends, an inlet and an outlet defined between each of the ends, and an interior. The valve assembly further includes a motor means such as a solenoid which is disposed at one of the ends, and an exit tube is defined at the other of the ends. Next a valve seal within the interior connects to and is operable by the motor means, the valve seal adapted to cycle within the interior and across the inlet or outlet. A controller circuit is then connected to the motor means for operating the solenoid incrementally. Therefore, upon activation of both the airflow generator and the controller circuit, pressurized air from the airflow generator continuously enters the inlet but passes out of the outlet only when the solenoid triggered by a flow sensor activates the valve seal to at least partially unblock the inlet such that the pressurized air is converted into a single, repeatable burst of air exiting the outlet. The valve seals can be configured in a variety of ways as long as some form of wall or solid end acts as a seal and a defined slot or opening allows airflow to incrementally pass out of the tube valve seal to thereby modify the traditional, constant airflow.

The associated method then for modifying airflow into a nasopharyngeal airway or trachea of a patient, comprises the steps of producing a constant head of pressurized airflow into a valve assembly attached to a patient via an air or gas tube, the valve assembly including a mid-operated valve seal and flow sensor; maintaining against the valve while the patient is exhaling and the valve is at rest, and, permitting the valve to incrementally retract and allow the airflow to pass through the valve assembly and into nasopharyngeal airway or trachea when the patient inhales, as a result converting the constant head of pressurized airflow into an assisted burst of gas given during inhalation while allowing the patient to finish inspiration and exhale against little or no pressure when the valve is at rest.

Figure 1:
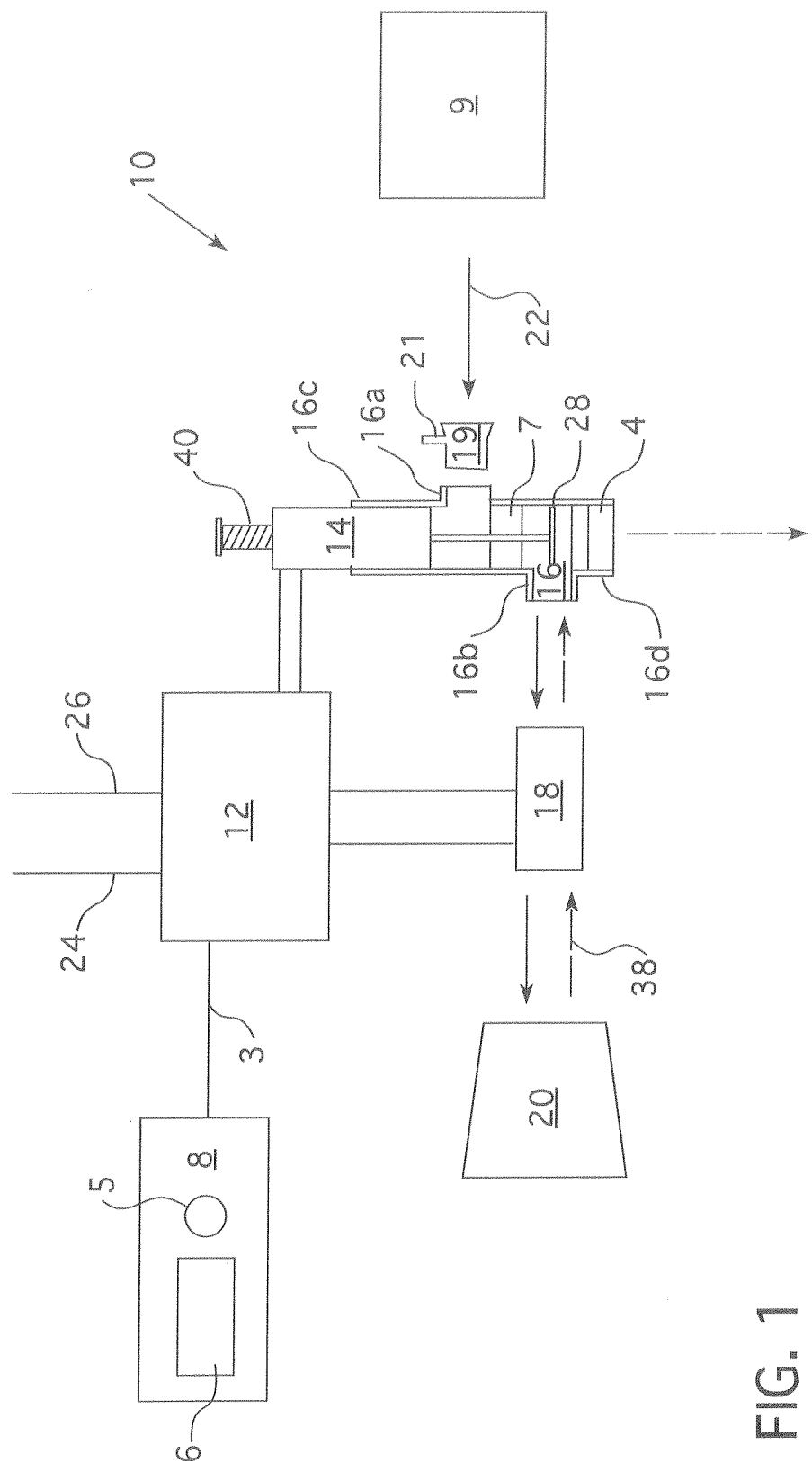
FIG. 1 shows a schematic representation and partial elevational view of the instant invention.

Dotted line arrows are shown to depict the direction of patient exhaled breath flow. Solid line arrows mark the air stream flow path of air drawn into the apparatus.

DETAILED DESCRIPTION OF THE PREFERRED EMBODIMENTS

The invention will now be described in detail in relation to a preferred embodiment and implementation thereof which is exemplary in nature and descriptively specific as disclosed. As is customary, it will be understood that no limitation of the scope of the invention is thereby intended. The invention encompasses such alterations and further modifications and applications as would normally occur to persons skilled in the art to which the invention relates. This detailed description of this invention is not meant to limit the invention, but is meant to provide a detailed disclosure of the best mode of practicing the invention.

With reference then to FIGS. 1-6, illustrated is an assembly 10 which includes valve assembly 16, a programmable controller circuit 12 encoded by programmer 8, a normally-open electrical switch/sensor 18, and a patient interface device 20 such as a mask, tracheal tube, nasal cannula or similar patient interface, and an optional drug delivery port 19.

Valve assembly 16 has two ends 16c, 16d, an inlet 16a, an outlet 16b, and an interior feed tube 7. Valve assembly 16 further includes an electromagnetic solenoid 14 typically disposed proximate end 16e, opposite exit tube 4, which is defined at end 16d. Instead of a solenoid 14 any type of motor means may be implemented such a stepping motor. Motor means as used herein therefore encompasses any type of motor, but preferably a solenoid 14.

The airflow generator 9, which is separate from and later attached to the device, may be in the form of a blower or fan of the type used to produce a pressurized airflow, hospital wall air or compressed bottled air or gas. Airflow generator or airflow generator means therefore is used herein to define any type of blower, fan, hospital wall air, compressed air, or any traditional positive airway pressure (PAP) device, including oxygen, already attached to the same. The solid line arrows mark the air stream flow path, beginning with air drawn into the apparatus from the airflow generator 9 as indicated by arrow 22.

The electric current to operate the apparatus is supplied through conductors 24 and 26, which also supply current to solenoid 14 and switch 18. The airflow generator 9 is intended to operate continuously whereby a constant head of pressurized air is maintained. However, the solenoid 14 is at rest and will permit full air passage there through to the valve assembly 16 only when the solenoid 14 is charged by switch 18.

The valve assembly 16 of FIG. 1 further includes a flexible or rigid valve seal 28 such as a circular disc, ball or joined split ball, with the flexible valve mounted to the plunger rod 11 of solenoid 14 plunger rod 11. In alternate, the use of a slotted tube within two additional separated tubes may act as a valve (not shown). Valve seal 28 is preferably seated within the interior feed tube 7 and is operable by solenoid 14, adapted to cycle within the feed tube 7 between solenoid 14 and exit tube 4, across outlet 16b. Valve seal 28 can alternatively be placed directly within exit tube 4, which would place valve seal 28 more proximate to end 16c, so use of "within feed tube 7" is meant to encompass any location throughout the interior of valve assembly 16 since exit tube 7 is formed within the interior of valve assembly 16. In its relaxed position (shown), the valve seal 28 will at least partially cover and seal the outlet 16b or aperture of the therapy airflow or end 16d of the exit tube. The valve seal 28, in this case, is a member which normally seals against the inside surface of the feed tube 7 but will open in response to airflow passing the switch (an attempt to inhale) which signals solenoid 14 to charge (not shown) and seal against the exit tube 4 which allows the airflow to pass through the valve arrangement out of outlet 16b, the switch and thence into the patient via a patient interface device 20. "Member" as used herein can mean any shape, e.g. circular, square, etc. depending on the inside surface of the feed tube 7 as long as the seal closes against the feed tube 7.

It should be noted that the patient interface 20 and valve assembly 16 will allo unassisted inhalation and exhalation by the patient to permit entry of ambient air when the valve is in the "at rest" position. The patient interface 20 is meant to be worn in sealed relation to a patient whereby ambient air during inhalation will pass into the patient interface past valve seal 28. Exhaled breath will pass through switch 18 whereby the breath flow will be in the direction of the dotted line arrow 38, and into the valve assembly 16. Exhaled breath pressure entering the valve assembly 16 passes by the valve seal 28 which is now closed and seated against the feed tube 7, and through exit tube 4 to ambient. A return spring 40 allows the solenoid plunger rod 11 to return to its original position upstream from said outlet 16b (towards inlet 16a). This return action of the solenoid sets the switch internally whereby, as the solenoid 14 relaxes, the valve seal 28 will return back to its original position and at the same time close off the release of pressurized air or gas to complete the electrical circuit to the solenoid 14. The solenoid 14 is thereby caused to cycle open and then re-close after having permitted a "burst" of pressurized air to move into the valve assembly 16 and past the valve seal 28 out of outlet 16b and past the switch 18 and into the patient interface 20. The pressurized airflow burst is directed into the nasopharyngeal airway or trachea of the patient as the patient's inhalation action occurs, and ambient air moves through valve 16 to allow the patient to complete the breath intake voluntarily. The subsequent exhalation by the patient repeats the described process whereby a pulse, burst of pressurized air is delivered to the patient interface 20 and thence to the patient's airway as a function of each breathing cycle. An additional feature triggers the pressurized gas flow by way of an adjustable timing device should the patient not attempt to inhale himself. It should be understood that "burst" used herein and in the claims refers to a burst or flow of air of any duration and degree. For example, the produced burst can emulate that of an MPAP, or Metered Positive Airway Pressure device, wherein the burst terminates and slowly dissipates in pressure. The burst an also emulate that of a bi-level design wherein the burst has two levels of constant pressure, namely a higher level of constant therapeutic pressure upon inhalation along with a constant lower level of therapeutic pressure upon exhalation.

The pressurized airflow burst is adjustable by way of the controller circuit 12 which is encoded by way of the programmer 8. The adjustments include, but are not limited to, ramp up time, length of burst, sensitivity of the switch/sensor, timed release of burst or any combination of these settings, should they be required. The programmer 8 is linked to the control circuit by way of a cable 3 which is rigidly connected to the programmer 8 but which is detachable from the control circuit 12. Once the preferred settings have been programmed into the control circuit they will remain fixed until changed by reconnecting the programming box 8 and the settings are adjusted to alternate values. The values appear on a viewing screen 6 nod are sot via a navigation button 5. An additional embodiment allows the programmer 8 and control circuit 12 to be combined into a single enclosure or with cable 3 rigidly connected to both the program box and the control circuit 12 for hospital use, EMS use, testing, etc. The valve assembly 10 is attached to a traditional CPAP unit or traditional constant airflow generator 9 as above, which will convert that traditional CPAP unit or traditional airflow generator into a device providing an intermittent and adjustable air stream (gas), into a therapeutic burst, puff, bolus or flow of air to a patient during inhalation. By this means the patient is able to receive an air supply or concentration of gas, given as a single, but repeatable dose to achieve an immediate effect in transit through assembly 10 and by way of patient interface 20. The system and method thus can be utilized with pre-existing airflow generation means already implemented in homes, centers and hospitals, thereby varying the traditional constant airflow with use of the instant accessory. An assisted burst of gas given during inhalation or inspiration at the beginning of each breath will prevent collapse or maintain the upper airway, reduce inspiratory WOB (work of breathing), reduce expiratory WOB and reduce or prevent the dryness related to continuous positive airway pressure. The assisted burst itself raises the concentration in the body to a therapeutic level while allowing comfort to the patient. This is accomplished to allow the patient to finish inspiration himself and to exhale against little or no therapeutic pressure. The bolus provided is adjustable and tapers off over a period of time during the inspiration cycle, thus allowing it to maintain positive pressure throughout most of the inhalation process which will promote gas exchange in the alveoli and also keep open smaller airways. A certain amount of natural resistance experienced upon exhale through the exhalation circuit. There may be times when a greater or therapeutic pressure upon exhale is desired or required, the use of devices such as a positive end-expiratory pressure (PEEP) valve may be added to tube 4 or by the addition of a similar restrictive device being incorporated or added into the breathing circuit. As above, should it be desirable, a continuous therapeutic flow of positive pressure air upon inhalation along with a lower level of therapeutic positive pressure airflow during exhalation could result.

In some cases additional medication is required. The installation of the optional drug delivery port 19 allows the introduction of inhalable medication. Because of the assembly 10 configuration, the delivery port can be added instantly without harm to the patient or alternatively it can be applied initially and with the entry port 21 being capped until needed.

As opposed to CPAP or continuous ventilation this method allows an infinite control of therapeutic air or gas flow during non invasive ventilation which is critical, especially in neonates. Assembly 10 provides the clinician a means of providing safety and comfort for those who cannot speak for themselves.

Although FIG. 1 broadly illustrates the underlying system and method of the present invention, the use of different valves, sensors and components are possible. In lieu of solenoid 14 a stepping motor or similar control (not shown) may be used to control the pressurized air/gas delivery by rotating a seal within valve assembly 16. However, additional components similar to those shown in FIG. 2 would be required.

Figure 2:
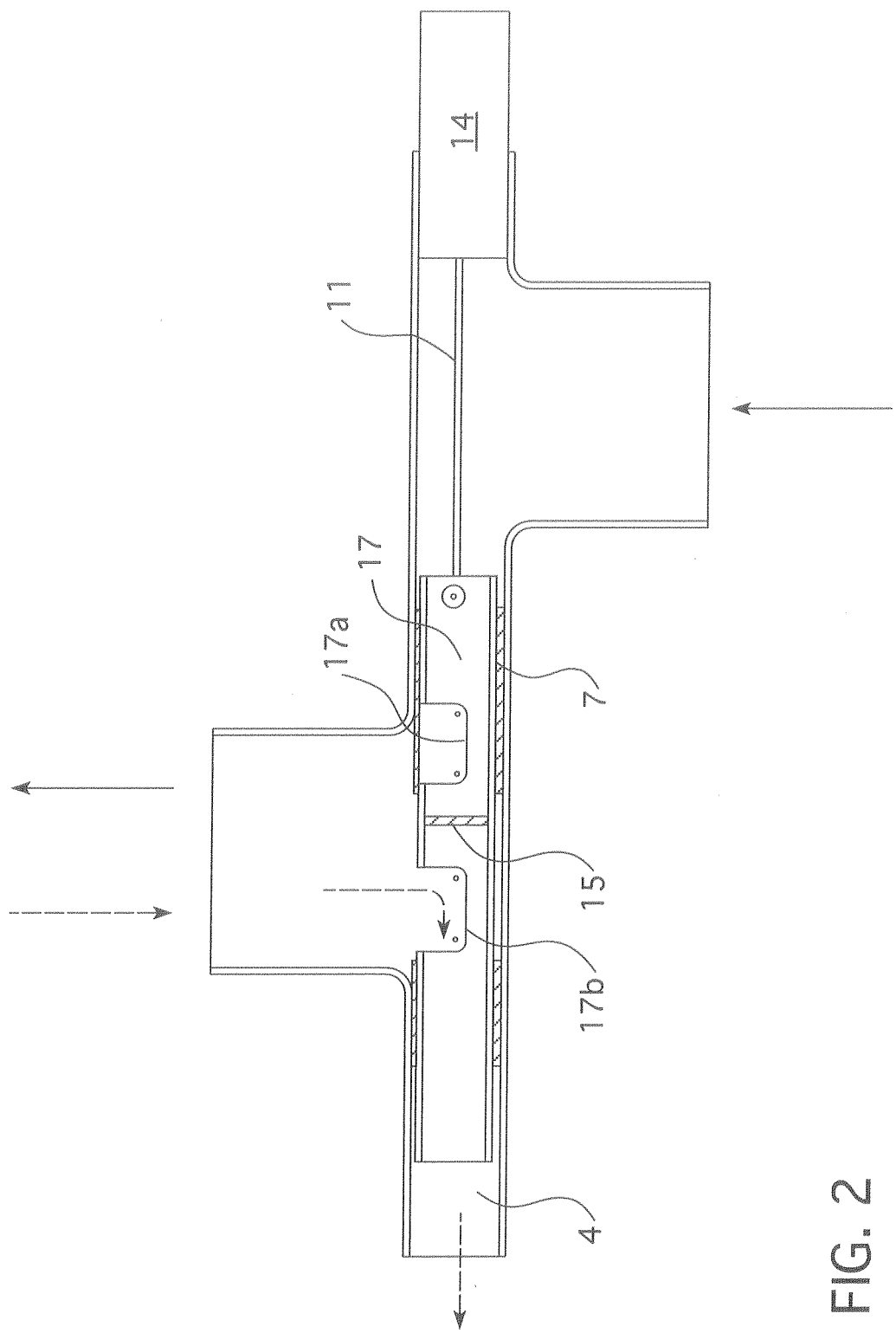
FIG. 2 shows an elevational view in partial section illustrating an alternative embodiment of the valve of the present invention.

FIG. 2 shows a sliding tube valve seal 17, whereby it replaces the above mentioned valve seal 28 with a slotted, hollow tube. The sliding tube valve seal 17 is connected to the solenoid valve 14 by way of plunger rod 11 and closes off air pressure when the solenoid 14 is relaxed as shown. At least one slot 17a is defined within the outer shell of the hollow tube. A seal or wall 15 positioned beyond slot 17a and within the sliding tube valve seal 17 directs the flow of air to the patient when the tube is pushed forward by the solenoid valve. In addition, the sliding tube valve seal 17 directs the flow of exhaled air from the patient through exit tube 4 to atmosphere. An additional hole or exhalation slot 17b or other means to allow the exhaled air to re-enter the hollow tube and proceed to exit tube 4 is defined on the other side of wall 15. The placement of the slots 17a, 17b in the tube may be adjustable or fixed in order to control both the inhalation and exhalation pressures. The sliding tube valve seal 17 slides freely within the feed tube 7 and exit tube 4 and is controlled by way of the solenoid 14.

In alternate, a second method and device for converting a constant airflow generator to a multi-level therapeutic device by way of assembly 10 attached to a CPAP unit or traditional constant airflow generator, 12 will convert a traditional CPAP unit or traditional airflow generator into a device providing an adjustable air stream or gas, into multiple pressurized therapeutic air flows and delivering them to a patient.

The device is able to deliver bi-level or multiple levels of therapeutic flows of air or gas to a patient. A patient may receive one or more levels of pressurized air upon inhalation and one or more lower levels of pressurized air upon exhalation. This may be accomplished in several ways such as by leaving valve 28 open or partially open at all times and regulating the distance between valve 28 and feed tube 7 during inhalation. Thus one or more elevated pressures is delivered to patient through assembly valve 16, switch 18 and patient interface 20 upon inhalation while bleeding off the excess air and pressure through tube 4. The valve 28 would then partially adjust to a predetermined position or predetermined positions for exhale creating a lower exhalation pressure or multiple lower exhalation pressures. This could allow a bleed off of air by way of tube 4. Although not necessary, for a split second valve 28 could close against feed tube 7 and start the cycle over or the—add on device could just switch back to the higher level upon inhalation.

As a third method and device, seal 28 could close off or partially close off against tube 4 during inhalation and then open the exit port for exhalation to release a predetermined amount of air flow and pressurized air to cause the required pressure drop. The process would then repeat itself as described previously.

Figure 3:
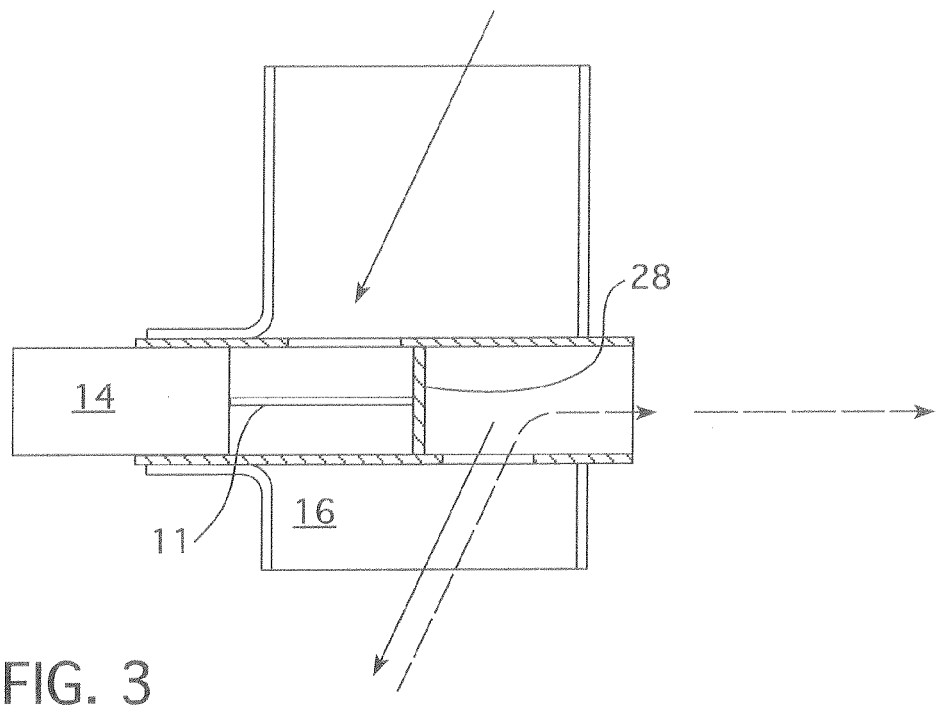
FIGS. 3 and 4 show elevational views in vertical section illustrating further embodiments of the apparatus valve of the present invention.
Figure 4:
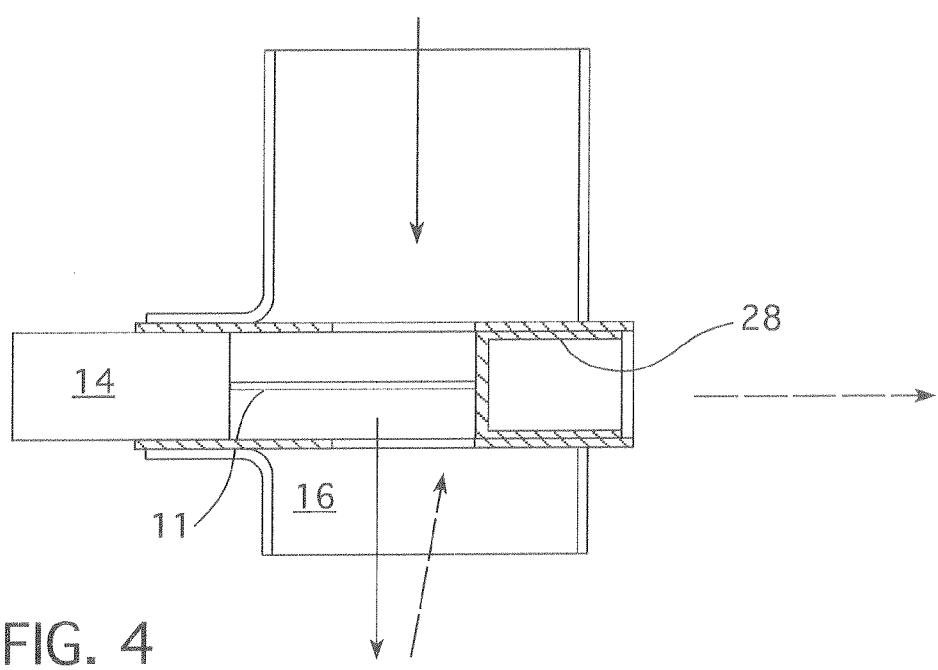

FIG. 3 and FIG. 4 illustrate smaller versions of the assembly 16 in that the airflow is controlled in a straight tube and components are more compact.

Figure 5:
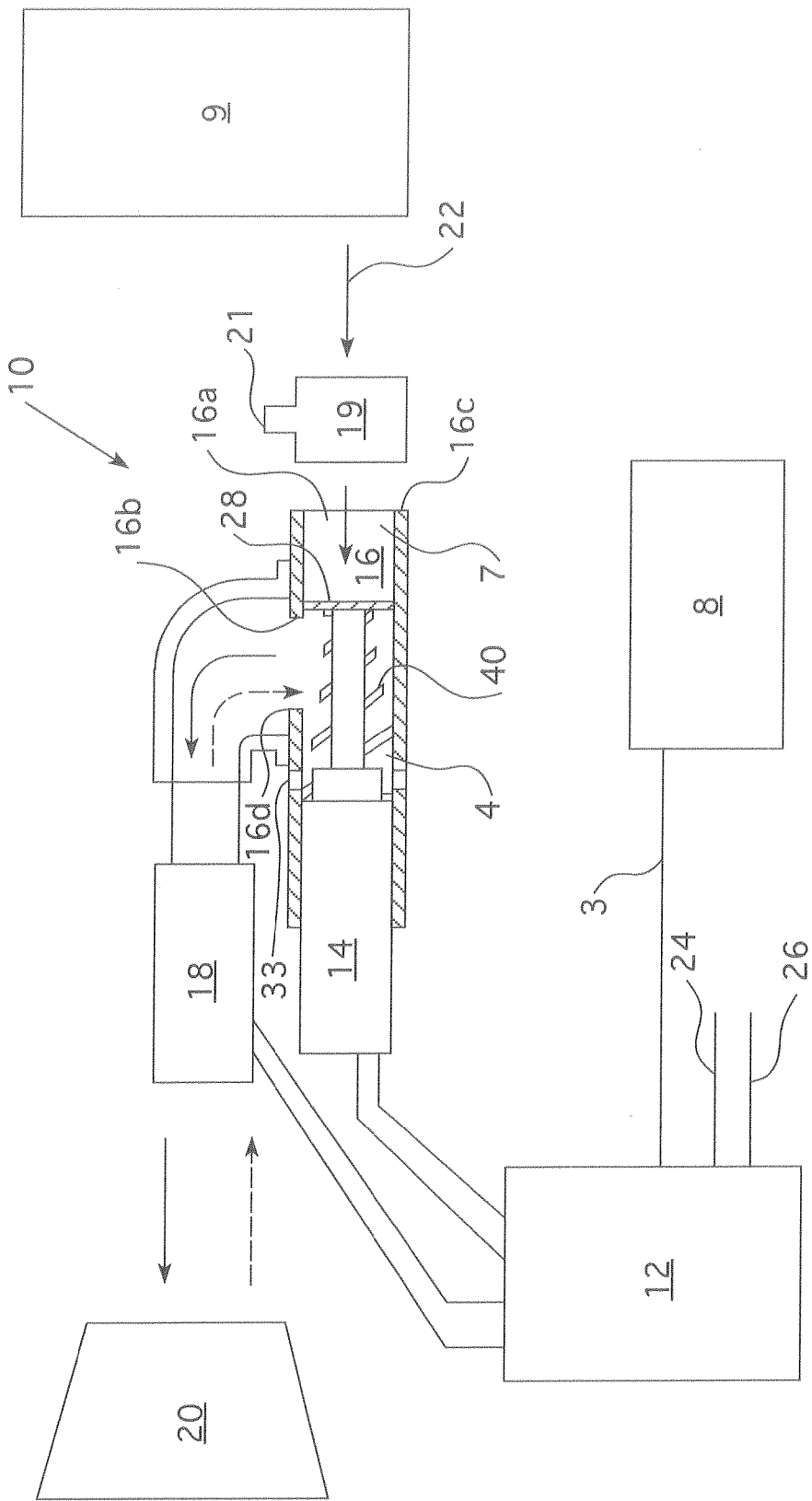
FIG. 5 shows an elevational view in vertical section illustrating still another alternative form of the system.
Figure 6:
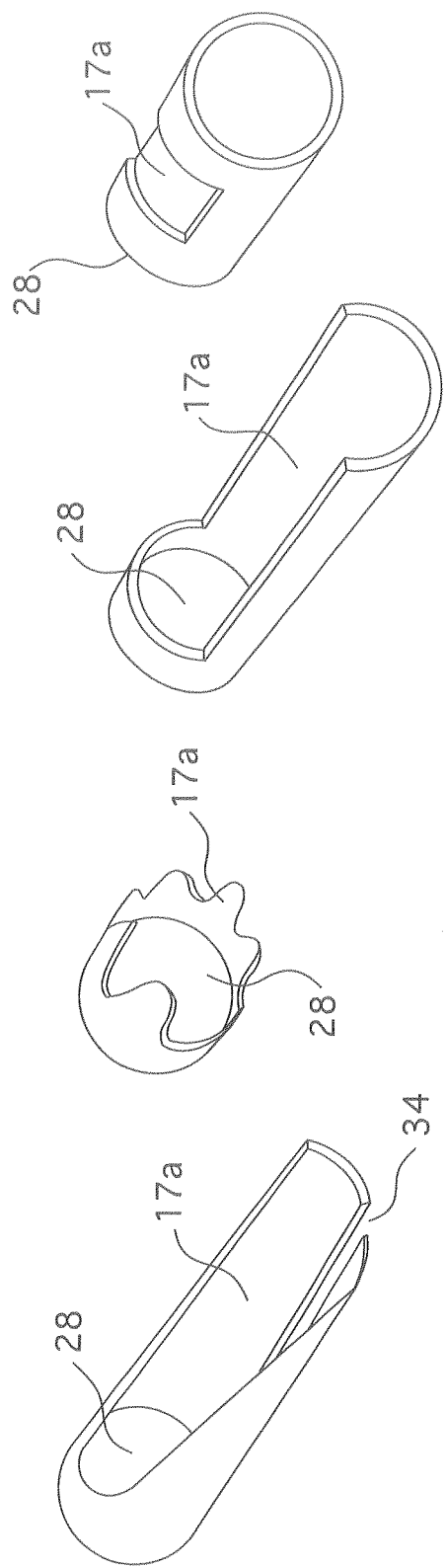
FIG. 6 shows perspective views of certain components intended for other valve embodiments.

FIG. 5 shows a fourth method and device wherein the return spring 40 may be positioned between the solenoid 14 and valve seal 28 and will be of sufficient strength to control the flow of air or gas coming from the constant air flow generator. In this embodiment the spring is compressed when the solenoid 14 is charged allowing the air flow and pressure to increase to a therapeutic level. When the solenoid 14 is at rest the air flow is restricted to a lower level or may be shut off completely. Ventilation holes 33 or slots, allow exhalation of the patient and provide ambient air should a power failure occur. In addition, these ventilation holes 33 may be restricted or sealed in order to regulate inhalation and/or exhalation pressure. As an alternate, (not shown) the return spring may be positioned within the solenoid itself between the back end of the solenoid and the tip of the plunger 11. Accordingly, "attached to" as used in relation to the spring and solenoid means the spring can be attached to the exterior of the solenoid or be integrated within the solenoid. As previously stated seal 28 could close off or partially close off against tube 4 during inhalation and then increase open the exit port for exhalation to release a predetermined amount of air flow and pressurized air to cause the required pressure drop. The process would then repeat itself as described previously.

In any of the apparatuses and methods above, the use of sliding tube valve seal 17 (slotted tube of FIG. 2) in place of the seal 28 is possible. Furthermore, with reference to FIG. 6, several controlling configurations as shown may be used in place of the sliding tube valve seal 17 in FIG. 2 or in place of valve seal 28 on FIG. 5. Any of the valve seals can be keyed by use of a slot 34 and guide. The guide may be a pin, key, roller or any variation of these. Accordingly, "tube valve seal" as defined herein means any shape of tube shown and described above and by the alternative embodiments of FIG. 6 and their obvious variations, the critical feature of which require some form of wall 28 or solid end to act as a seal and a defined slot 17a (FIG. 2) opening to allow airflow to pass out of the tube valve seal. As in the first method the valve seal 28 can be a circular soft or rigid member which normally seals against the inside surface of the feed tube 16 on FIG. 5. The seal mates against or close to the face of a now split or two piece tube (not shown) but will respond to airflow passing the switch (an attempt to inhale) which signals solenoid 31 to charge (not shown) which allows the airflow to pass through the valve arrangement out of outlet 16b, the switch 18 and thence into the patient via a patient interface device 20. In alternate, solenoid 14 may also be made to respond to exhalation when continuous airflow during inhalation is present. In such a case valve 28 is will regulate the airflow in relation to exit tube 4.

In the above embodiments the valve seal and tube valve seal move laterally within or against the feed tube (or the exit tube). It should be understood that another seal embodiment may be a butterfly valve intended to accomplish the same results, however in this embodiment the valve would move a quarter-turn rotationally. Therefore, in either instance of the valve seal, tube valve seal, or butterfly valve, as used in the claims, the valve will cycle back and forth in relation to the outlet and exit tube and "cycle" either laterally or rotationally.

I claim:

1. An assembly for modifying airflow into a nasopharyngeal airway or trachea of a patient, comprising:
a valve assembly adapted to attach to an airflow generator, wherein said airflow generator is a continuous blower of a type producing a constant head of pressurized air, said valve assembly having two ends, an inlet and an outlet defined between each of said ends, and an interior feed tube, said valve assembly further comprising:
a motor means signaled by said airflow disposed at one of said ends;
an exit tube defined at the other of said ends;
a valve seal within said interior feed tube connected to and operable by said motor means, said valve seal having defined therein a slot and further including an internal wall having a first side positioned beyond said slot, said valve seal adapted to cycle within said interior feed tube between said motor means and said exit tube and across said outlet;
an exhalation slot defined on a different side of said internal wall for allowing exhaled air from said patient to re-enter said interior feed tube and proceed to said exit tube;
a controller circuit connecting to said motor means for operating said motor means incrementally; and,
wherein upon activation of both said airflow generator and said controller circuit, pressurized air from said airflow generator continuously enters said interior feed tube from said inlet but passes out of said outlet only when said motor means causes said valve seal to move in relation to said exit tube to at least partially unblock said outlet such that said pressurized air is converted into a single, repeatable burst exiting said outlet.

2. The assembly of claim 1, wherein said valve seal is a shaped member which seals against an inside surface of said interior feed tube.

3. The assembly of claim 1, wherein said valve seal is a sliding tube valve seal.

4. The assembly of claim 1, further comprising a return spring attached to said motor means for returning said valve seal to a rest position downstream from said outlet.

5. The assembly of claim 4, wherein said spring is attached solely to said motor means at an end thereof.

6. The assembly of claim 4, wherein said spring is positioned between said motor means and said valve seal.

7. The assembly of claim 6, wherein ventilation holes are defined through said interior feed tube beyond said outlet and in front of said motor means.

8. The assembly of claim 1, further comprising a drug delivery port connected to said inlet through which said pressurized air passes and into which an inhalable medication can be received.

9. The assembly of claim 1, wherein said valve assembly further includes a plunger rod extending said valve seal from said motor means.

10. The assembly of claim 1, further comprising an electrical switch connected to said outlet and to said controller circuit for charging said motor means.

11. The assembly of claim 10, further comprising a patient interface device connected to said switch for receiving said repeatable burst from said outlet.

12. The assembly of claim 1, further comprising a programmer linked to and encoding said controller circuit for adjusting said single, repeatable burst.

13. A method for modifying airflow into a nasopharyngeal airway or trachea of a patient, comprising the steps of:
attaching a valve assembly having two ends, an inlet and an outlet defined between each end, and an interior feed tube to an airflow generator, wherein said airflow generator is a continuous blower producing a constant head of pressurized airflow into said valve assembly, said valve assembly including a solenoid-operated valve seal within said interior feed tube signaled by said airflow disposed at one of said ends; an exit tube defined at the other of said ends said solenoid-operated valve seal having defined therein a slot and further including an internal wall having a first side positioned beyond said slot; an exhalation slot defined on another side of said internal wall for allowing exhaled air from said patient to re-enter said interior feed tube and proceed to said exit tube;

attaching said valve assembly to a patient;

maintaining said airflow against said valve while said patient is exhaling and said valve is at rest;

permitting said solenoid-operated valve seal to incrementally retract and allow said airflow to pass through said valve assembly and into said nasopharyngeal airway or trachea when said patient inhales; and, permitting exhaled air from said patient to re-enter said valve assembly and exit therethrough, as a result converting said constant head of pressurized airflow into an assisted burst of gas given during inhalation while allowing said patient to finish inspiration and exhale against lower or no pressure when said solenoid-operated valve seal is at rest.

14. The method of claim 13, further comprising the step of adjusting said assisted burst.

15. The method of claim 13, further comprising the step of delivering medication to said patient when said patient inhales.

16. The method of claim 13, further comprising the step of allowing said patient to intake ambient air when said valve is at rest.

* * * * *